United States Patent
De Crevoisier et al.

(10) Patent No.: US 9,873,002 B2
(45) Date of Patent: Jan. 23, 2018

(54) METHOD OF EVALUATING A PROCEDURE FOR DETERMINING THE AGGREGATE DOSE RECEIVED IN THE COURSE OF A RADIOTHERAPY TREATMENT

(71) Applicant: Universite De Rennes 1, Rennes (FR)

(72) Inventors: Renaud De Crevoisier, Rennes (FR); Pascal Haigron, Rennes (FR); Antoine Simon, Rennes (FR); Guillaume Cazoulat, Rennes (FR); Aurelien Dumenil, Rennes (FR)

(73) Assignee: UNIVERSITE DE RENNES 1, Rennes (FR)

( * ) Notice: Subject to any disclaimer, the term of this patent is extended or adjusted under 35 U.S.C. 154(b) by 0 days.

(21) Appl. No.: 14/431,598

(22) PCT Filed: Sep. 26, 2013

(86) PCT No.: PCT/EP2013/070027
§ 371 (c)(1),
(2) Date: Mar. 26, 2015

(87) PCT Pub. No.: WO2014/049030
PCT Pub. Date: Apr. 3, 2014

(65) Prior Publication Data
US 2015/0251017 A1 Sep. 10, 2015

(30) Foreign Application Priority Data
Sep. 26, 2012 (FR) .................................... 12 59054

(51) Int. Cl.
*A61N 5/10* (2006.01)
(52) U.S. Cl.
CPC ......... *A61N 5/1031* (2013.01); *A61N 5/1071* (2013.01); *A61N 5/1075* (2013.01);
(Continued)

(58) Field of Classification Search
CPC .... A61N 5/103; A61N 5/1031; A61N 5/1071; G06T 7/0089; G06T 2207/30004
See application file for complete search history.

(56) References Cited

U.S. PATENT DOCUMENTS

2014/0005464 A1* 1/2014 Bharat et al. ..................... 600/1

FOREIGN PATENT DOCUMENTS

WO 2012123894 A1 9/2012

OTHER PUBLICATIONS

English translation of IPRP, dated Mar. 26, 2015 for corresponding International Patent Application No. PCT/EP2013/070027, filed Sep. 26, 2013.

(Continued)

*Primary Examiner* — David Porta
*Assistant Examiner* — Faye Boosalis
(74) *Attorney, Agent, or Firm* — David D. Brush; Westman Champlin & Koehler, P.A.

(57) ABSTRACT

A method is provided for evaluating a procedure for determining an aggregate radiotherapy dose received in the course of a radiotherapy treatment. The method includes: defining a deformable model of at least one organ to be treated and of at least one neighboring organ, generating a series of simulated images, interpretable by the procedure to be evaluated, with aid of the model; comparing the aggregate dose calculated by the procedure to be evaluated, applied to at least one of the simulated images, with a reference aggregate dose, so as to deliver at least one item of information representative of the quality of the procedure, the reference aggregate dose being obtained by taking into account anatomical deformations applied to the organs, so as to determine a reference dose actually received at each treatment session by the organs, as a function of their actual shape and/or actual position during this session.

13 Claims, 3 Drawing Sheets

(52) U.S. Cl.
CPC ............... *A61N 2005/1072* (2013.01); *A61N 2005/1076* (2013.01)

(56) References Cited

OTHER PUBLICATIONS

Miyabe Yuki et al: "New algorithm to simulate organ movement and deformation for four-dimensional dose calculation based on a three-dimensional CT and fluoroscopy of the thorax", Medical Physics, vol. 36, No. 10, Sep. 4, 2009 (Sep. 4, 2009), pp. 4328-4339, XP012129704, AIP, Melville, NY, US.

Wen Ning et al: "Evaluation of the deformation and corresponding dosimetric implications in prostate cancer treatment", Physics in Medicine and Biology, vol. 57, No. 17, Sep. 7, 2012 (Sep. 7, 2012), pp. 5361-5379, XP002693995.

French Search Report and Written Opinion dated Mar. 22, 2013 for corresponding French Patent Application No. 1259054, filed Sep. 26, 2012.

English translation of the International Search Report dated Apr. 3, 2014 for corresponding International Application No. PCT/EP2013/070027, filed Sep. 26, 2013.

\* cited by examiner

METHOD OF EVALUATING A PROCEDURE FOR DETERMINING THE AGGREGATE DOSE RECEIVED IN THE COURSE OF A RADIOTHERAPY TREATMENT

1. CROSS-REFERENCE TO RELATED APPLICATIONS

This Application is a Section 371 National Stage Application of International Application No. PCT/EP2013/070027, filed Sep. 26, 2013, the content of which is incorporated herein by reference in its entirety, and published as WO 2014/049030 on Apr. 3, 2014, not in English.

2. FIELD OF THE INVENTION

The field of the invention is that of radiotherapy, and in particular, that of determining the radiation doses received by organs during radiotherapy.

More specifically, the invention relates to quality controls on a procedure for calculating an aggregate dose implemented by a predefined radiotherapy system.

3. PRIOR ART AND DRAWBACKS

It is known that there are several types of treatment for cancer, among which radiotherapy occupies an essential place. Thus, in France, about 280,000 cancers are diagnosed per year, 200,000 of them being treated, at least partly, by radiotherapy.

External radiotherapy, to which the invention applies, implements a linear accelerator, placed at about one meter from the patient. The accelerator generates radiation beams (photons, electrons or protons, depending on the techniques implemented) that converge towards the tumor and deliver a relatively homogenous dose of radiation in the zone of intersection of the beams.

Radiotherapy applies potentially dangerous radiation which must therefore be controlled with precision with respect to both the aggregate dose received by the organ to be treated and the doses inevitably received by neighboring healthy organs (which of course need to be minimized).

Radiotherapy treatment relies especially on a preliminary phase of planning or scheduling during which the radiation ballistics (the parameters of the linear accelerator) are determined. The dose that will theoretically be received by the organs is then computed. This step relies on the acquisition of a scanner image used to visualize the tumor target and the organs at risk. The treatment is therefore planned according to a fixed configuration of the organs (in terms of size and shape).

However, during the treatment, which is sub-divided into sessions (for example 40 sessions for cancer of the prostate), these organs (for example the bladder and rectum for cancer of the prostate) get deformed. The dose that they receive is then different from the planned dose.

In order to estimate the aggregate dose received by the organs during the different fractions (sessions) of treatment, procedures relying on the estimation of the deformation of the organs are proposed. These procedures rely on embedded imaging (for example of the CBCT type) to visualize the organs during each fraction. Image registration procedures (applied between the CBCTs and planning scanner) enable the estimation of the deformations, which are then applied to the daily dose, so as to propagate the dose delivered on the planning scanner and so as to be thus able to totalize the dose.

Different procedures for computing the aggregate dose are proposed but the problem of quality control over these procedures remains unresolved. Indeed, these are theoretical procedures and there are no existing means for the in situ measurement of the doses really received by each organ.

Indeed, these procedures rely on an image-registration step that gives an estimation of the deformation of the organs between the fractions of treatment. This estimation produces instances of local imprecision as regards amplitude and localization that vary according to the algorithm and the images considered. Now, this variability of amplitude and localization in the imprecision of registration has a major impact on the quality of the estimated aggregate dose. For example, an imprecision of the localized registration in an anatomical region associated with a uniform dose will result in a very limited error of aggregate dose as compared with imprecision of localized registration in a zone with a high dose gradient.

Apart from the precision of the deformation fields, it is vital to evaluate the procedures for computing the aggregated dose in terms of dosimetry.

4. SUMMARY OF THE INVENTION

An aspect of the present disclosure is directed to a method for evaluating a procedure for determining the aggregate dose received during a radiotherapy treatment, called a procedure to be evaluated.

According to the invention:
a deformable model is defined for at least one organ to be treated and at least one neighboring organ, and by means of said model, a series of simulated images interpretable by the procedure for evaluating is generated;
the aggregate dose computed by the method for evaluating, applied to at least one of said simulated images, is compared with an reference aggregate dose, so as to deliver at least one piece of information representing the quality of said method,
said reference aggregate dose being obtained in taking account of anatomical deformations applied to said organs so as to determine a reference dose effectively received by said organs at each session of treatment as a function of their shape and/or their real position during this session.

Thus, the invention proposes an efficacious approach to estimating a reference aggregate dose taking account of the deformations of the organs between the fractions of treatment. Indeed, in taking account of these deformations, a precise estimation is available of the real dose that would be received by this model. Then, in considering data coming from this model as input data of the method for evaluating, the aggregate dose determined by this method is available. It is then possible to compare this aggregate dose with the reference aggregate dose, and therefore objectively and precisely evaluate the quality of the method for evaluating.

According to one particular embodiment of the invention, obtaining said reference aggregate dose implements the following steps:
generating a model comprising at least one organ to be treated and at least one neighboring organ;
determining a field of deformation of said organs from at least one rule of deformation and/or progress of said organ;
obtaining a series of images of said model at different instants, called simulated images, comprising at least one image representing a planning scanner and a series of tracking images each corresponding to a session of treatment;

planning a treatment on the basis of at least one of said simulated images by means of a treatment planning system implementing said procedure for determining radiotherapy doses so as to obtain a planned dose and parameters of a set of radiation ballistics;

determining one set of doses per fraction, each corresponding to one of said sessions;

determining said reference aggregate dose in applying said deformation field to each tracking image so as to determine said effectively received reference dose.

Said step for generating a model can especially deliver a finite-elements model in the form of a 3D mesh.

Said step for determining a field of deformation can especially implement deformations representing the elasticity of each organ, defined by a law of behavior of materials, for example a hyperelastic model.

In addition, said deformations advantageously take account of the possible contacts between said organs.

Said step for obtaining a series of simulated images can especially associate, for each simulated image, a view of said model and a possibly simplified image of a real patient in order to take account of at least the bone structure of this patient.

According to one implementation of the invention, during said step for determining said reference aggregate dose, the dose associated with each tracking image considered is deformed along the simulated field of deformations so as to propagate said dose towards the space of the reference scanner, and all the propagated doses are summed up to obtain the reference aggregate dose.

Said piece or pieces of information representing the quality of said method for evaluating can especially belong to the group comprising:

an error of estimation of the aggregate dose at each point of the field of deformations, for example in the form of a 3D representation of the errors;

statistical measurements on the errors of estimation of the aggregate dose, such as average, minimum and maximum errors, standard deviation errors;

a representation of the estimated and reference aggregate doses in the form of dose-volume histograms;

statistical measurements from the dose-volume histograms such as average, minimum, maximum differences, sums of the differences;

differences in terms of indices for evaluating a treatment such as an average dose, a uniform equivalent dose, predictive values of tumoral control or toxicity.

In one particular embodiment of the invention, said organ to be treated belongs to the group comprising the prostate, the rectum, the bladder and the anal canal.

The invention also pertains to a computer program product downloadable from a communications network and/or stored on a computer-readable medium and/or executable by microprocessor, comprising a program code instructions to execute the method for evaluating as described here above and here below when it is executed on a computer.

5. LIST OF FIGURES

Other features and advantages of the invention shall appear more clearly from the following description of embodiments of the invention given by way of an illustrative and non-exhaustive example and accompanied by the drawings, of which:

6. DESCRIPTION OF ONE EMBODIMENT OF THE INVENTION 6.0 Introduction

The invention therefore proposes a method for evaluating, enabling especially quality control over the computation of the aggregate dose in radiotherapy determined by a procedure for determining doses to be evaluated (be it a known procedure, for example one implemented in present systems, or a future procedure).

The solution relies on a generation of digital simulation data based on a mechanical modeling of the behavior of the organs. A "finite elements" type of realistic model is deformed according to the mechanical characteristics of the organs. This approach makes it possible to have specific knowledge of the local correspondence of the organs and therefore to obtain a reference aggregate dose. By applying the procedures for computing the aggregate dose to this simulated data, it is possible therefore, for each procedure, to provide measurements evaluating the quality of its result.

The approach of the invention therefore relies on two phases:

the generation of a digital model or phantom corresponding to the anatomical region considered and the computation of the reference aggregate dose on this phantom;

the evaluation of procedures for computing the aggregate dose by use of the digital phantom as a reference.

The model relies on the generation of synthetic data coming from an FEM digital simulation based on a mechanical modeling of the behavior of the organs. A finite-element model of a realistic shape is generated and deformed according to the mechanical characteristics of the organs. A certain number of anatomical configurations are thus obtained. This approach thus makes it possible to have precise knowledge of the local correspondences of the organs.

The meshes obtained are then inserted into 3D images to obtain simulated images corresponding firstly to the planning image and secondly to the tracking images.

On the planning image, the ballistics are optimized, giving a 3D dose matrix corresponding to the planned dose. In addition, the dose for each tracking image or daily dose matrix is computed according to the planned ballistics. Depending on the daily dose matrices and the known deformations of the organs, the reference aggregate dose is computed.

6.1 Generation of the Model and Computation of the Reference Aggregate Dose.

Figure 1:
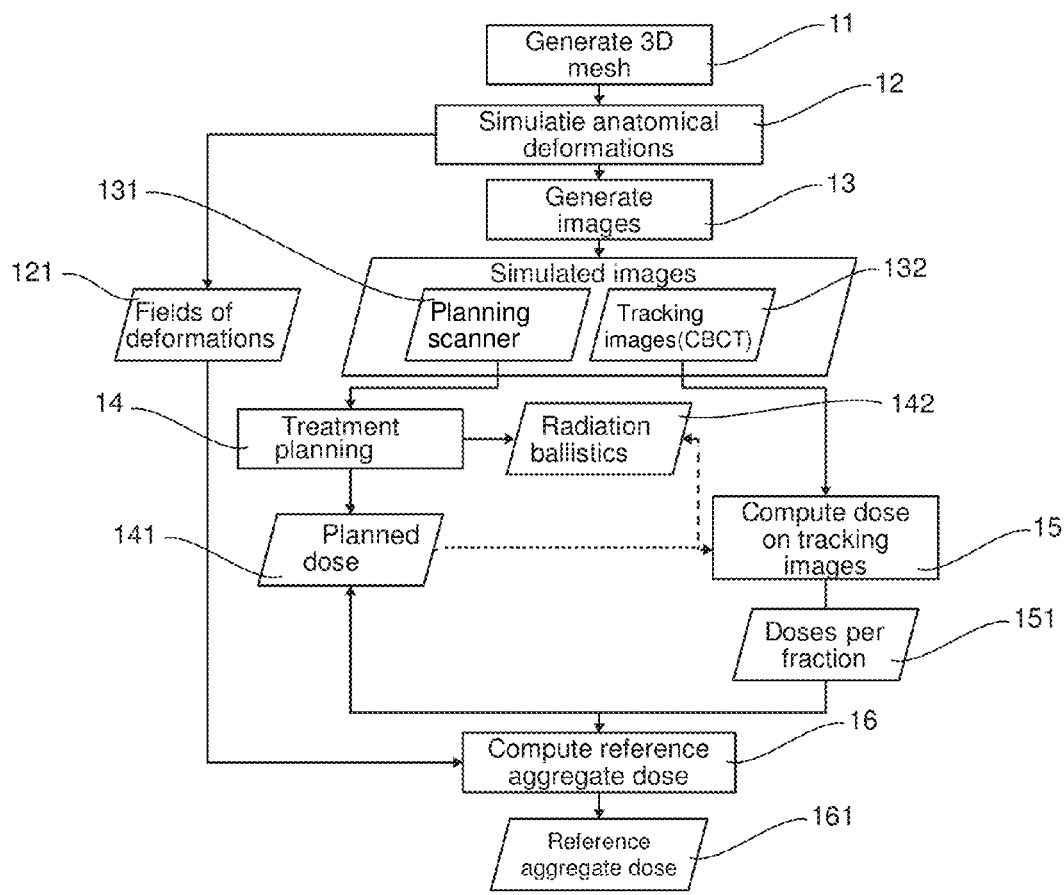
FIG. 1 is a block diagram providing a simplified illustration of the determining of an reference aggregate dose according to one embodiment of the invention.

The invention, according to the embodiment described here below, implements a generation of synthetic data coming from a digital simulation by finite elements based on a mechanical modeling of the behavior of the organs. The different steps of the generating of the simulated data are represented by FIG. 1 and described here below.

6.1.1 Generation of the 3D Mesh (11)

Figures 2A, 2B:
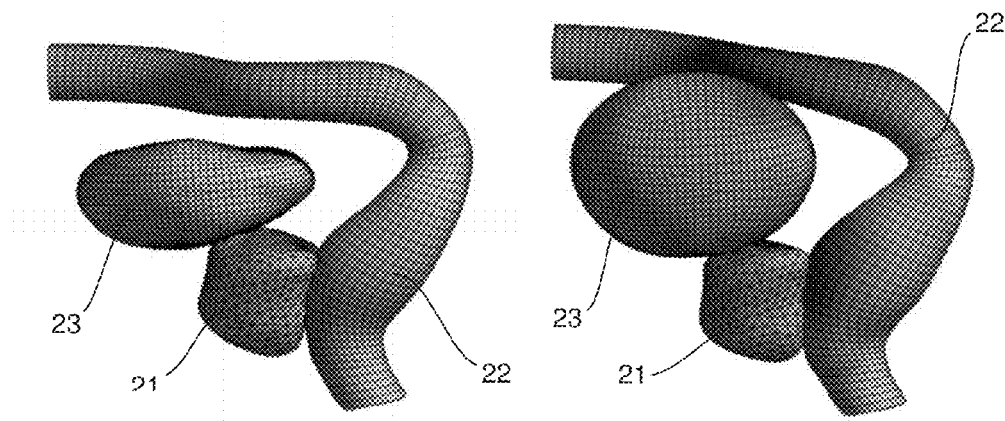
FIGS. 2A and 2B are an example of a model implemented according to the invention representing the pelvis in an initial state before deformation (FIG. 2A) and after an example of deformation (FIG. 2B)

A finite-element model of the organs considered is generated initially. This model represents the target organ and the surrounding organs at risk (for example the prostate 21, the rectum 22, the bladder 23 for the pelvis, as illustrated in FIGS. 2A and 2B).

The geometry of the anatomical structures of these different organs is defined either by considering typical volumes and shapes, or directly from images acquired on one or more patients. These geometries are represented by surfaces and/or volumes. Depending on the geometry of the organs, they can be either generated directly in considering B-splines modeling the contours of the organs (for example the rectum) or by making a geometrical shape that is discretized on surface (for example the bladder), or in volume (for example the prostate), depending on the nature of the organs (hollow or solid organs).

6.1.2 Simulation of the Anatomical Deformations (12)

The simulation of the deformations is done, in this embodiment, in considering properties of classic materials, (from the literature and/or from measurements) in terms for example of Young's modulus and Poisson's coefficient. Similarly, the thicknesses of the walls of the hollow organs (for example the bladder and the rectum) as well as their initial internal pressure are set at classic values.

An elastic linear relationship is used to describe the behavior of the prostate and the seminal vesicles with a Young's modulus value of 60 kPa and a Poisson's coefficient value of 0.495. An Ogden hyperelastic model is defined for the rectum (and the sigmoid colon) and the bladder, as illustrated in an example in the following table, for the case of the pelvis.

| Organ | Ogden model μ | Exponential coefficient α | Wall thickness (mm) | Pressure |
|---|---|---|---|---|
| Rectum | 0.0424 | 14.598 | 2.28 | 0 to 2 kPa |
| Bladder | 0.0412 | 6.767 | 2.9 | 0 to 5 kPa |

Boundary conditions are also defined, for example by fixing the extremities of the organs (rectum and apex of the prostate) and/or by defining elastic lengths (to represent the interactions of the organs considered with their environment). In addition, the contacts between the organs of interest can be defined.

The deformations of the organs are thus simulated according to the mechanical behavior modeled. For example, in the case of the pelvis, different values of internal pressure of the rectum and the bladder are applied to deform the structures with an amplitude comparable to that observed in the patient in different fractions of treatment. One example of a result of simulation of the deformations is shown in FIG. 2B. This FIG. 2B shows that the different organs can get deformed and move considerably, and that it is therefore essential to take account of this parameter to know the aggregate dose really received by each organ.

According to this procedure, a field of deformation 121 corresponding to the movement of each element of the model is known.

6.1.3 Generation of the Images

For each configuration of the organs considered in the modeling, an image is simulated. This image corresponds either to a scanner image 131 (to represent the scanner used during the planning or a tracking image, for example in the case of or to an image 132, made during treatment, enabling a viewing of soft tissues being irradiated. According to the embodiment illustrated, these are CBCT (Cone Beam Computed Tomography) images 132 to represent for example a tracking image in the case of the pelvis. Other types of images 132 can be used, for example tomography images.

Figure 3:
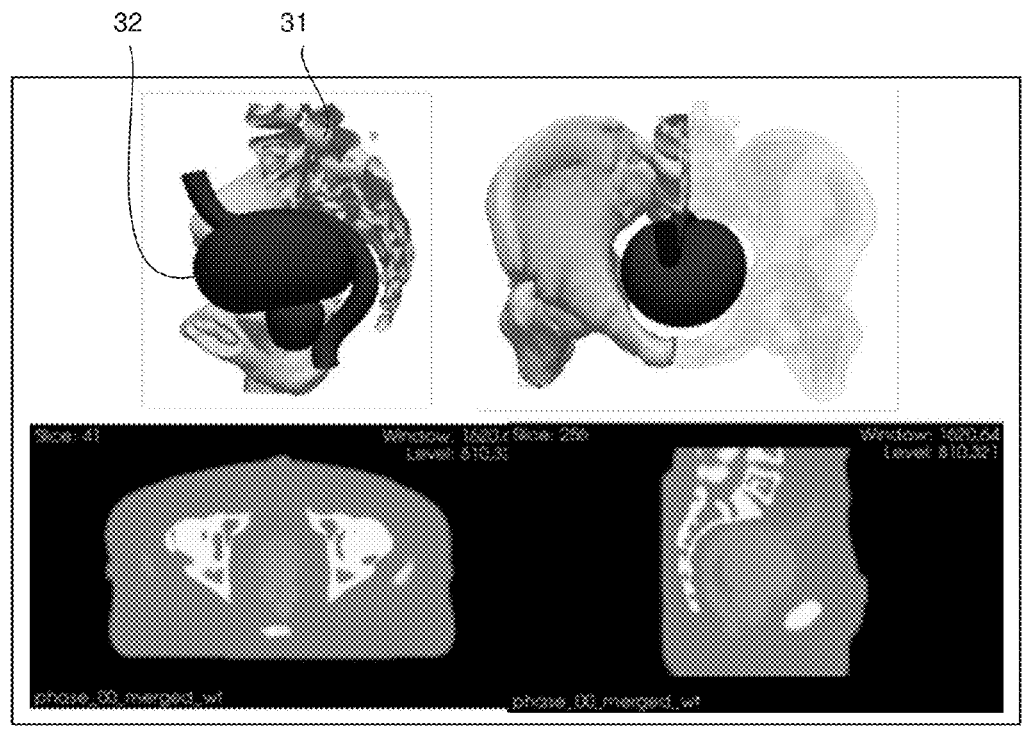
FIG. 3 is an example of insertion of an image coming from the model of FIG. 2A into data of a patient.
Figure 4:
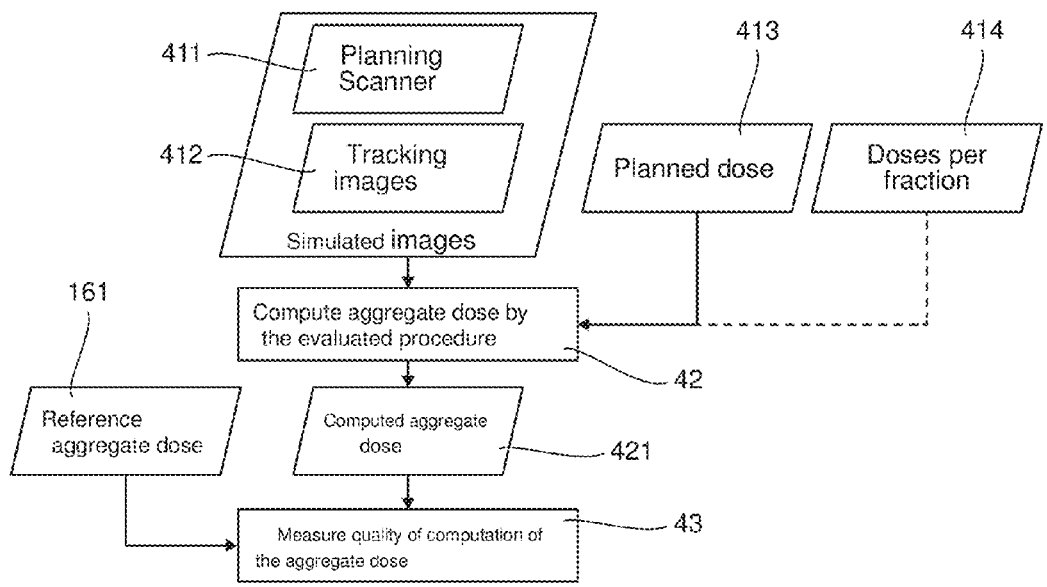
FIG. 4 is a block diagram providing a simplified illustration of evaluation of a procedure for evaluating using a reference aggregate dose determined according to the approach of FIG. 1.

To this end, as illustrated in FIG. 3, a scanner image or CBCT image 31 of a real patient is chosen and simplified (for example only the external contour and the bone structures are kept) and the geometrical models 32 are inserted therein in taking account of the intensities, textures and noise that are classic for the organs and images considered.

6.1.4 Planning of Treatment (14)

The images thus simulated, corresponding to planning images (scanner images) 131 are integrated into a commercially available treatment planning system (TPS), for example the Pinnacle system by Philips (registered trademark).

A reference treatment is planned (14). For example, for the pelvis, a planning is done for a total dose of 80 Gray in the prostate, using an IMCR (intensity-modulated conformal radiotherapy) technique. This ballistics optimizing phase gives the reference planned dose 141 associated with the planning scanner and the parameters of the radiation ballistics 142.

6.1.5 Computation of the Dose in the Tracking Images (15)

The dose 151 associated with the tracking images (corresponding to the dose really received by the patients during the radiation session at which the tracking image was acquired), called doses per fraction, is computed.

Two options can then be considered depending on the localization considered, as the case may be:
(i) the patient's external contours undergo little modification during the treatment (the case of the pelvis), and the planned dose can then be directly carried to the tracking image;
(ii) the patient's external contours are modified (for example following tumor reduction in ENT), the dose must then be recomputed (for example on a TPS) according to the planned radiation ballistics.

In both cases, a translation of the dose can be applied in order to take account of the repositioning of the patient (for example a rigid registration according to the position of the prostate).

6.1.6 Computation of the Reference Aggregate Dose (16)

With the deformation fields 121 between the planning image and the tracking images being known, along with the planned dose 141 and/or the dose associated with the tracking image 151, the reference aggregate dose can be computed (16).

For each tracking image considered, the associated dose is deformed according to the deformation field simulated. The dose is thus propagated towards the space of the reference scanner and can therefore be aggregated in this space.

This propagation is done for each tracking image and all the propagated doses are summed up to obtain the reference aggregate dose 161.

More specifically, the field of deformations is formed by a set of vectors defined at each node of the meshes describing the organs in their reference configuration. This deformation field spatially places the position of each node of a mesh in correspondence with its position after deformation. This deformation field, which is of low density, can be used as it is to aggregate the doses in the nodes of the mesh or it can be interpolated in order to aggregate the doses at each point of the volume. If the coordinates of a deformed point do not correspond to the sampling grid of the planning image, the dose can be interpolated.

6.2 Application of the Digital Phantom

The preliminarily simulated digital phantom data (data on planning images 411 and tracking images (for example CBCT images) 412, planned dose 413, and as the case may be doses per fraction 434) are given (42) to the evaluated tool which estimates the aggregate dose 421 received by the organs according to the method for evaluating.

This estimated aggregate dose 421 is compared (43) with the reference aggregate dose 161 determined according to the invention as described here above, and measurements of compliance are generated.

These measurements can be of different kinds, depending on requirements and comprise especially:
- an error of estimation of the aggregate dose at each point of the deformation field: 3D representation of errors;
- statistical measurements of the errors of estimation of the aggregate dose (mean, minimum and maximum errors, standard deviation errors, etc);
- a representation of the estimated and reference aggregate doses in the form of dose-volume histograms (DVH, reference mode of representation for evaluating the dose in clinical routine conditions. This corresponds, for an organ, to its fraction of the volume receiving at least one given dose);
- statistical measurements from the DVHs (mean, minimum, maximum differences, sum of the differences, etc);
- differences in terms of indices of evaluation (average dose, equivalent uniform dose (EUD), predictive values of tumor control or toxicity (TCP "tumor control probability"; NTCP "normal tissue complexity probability"), classical indices for evaluating DVHs.

Figure 5:
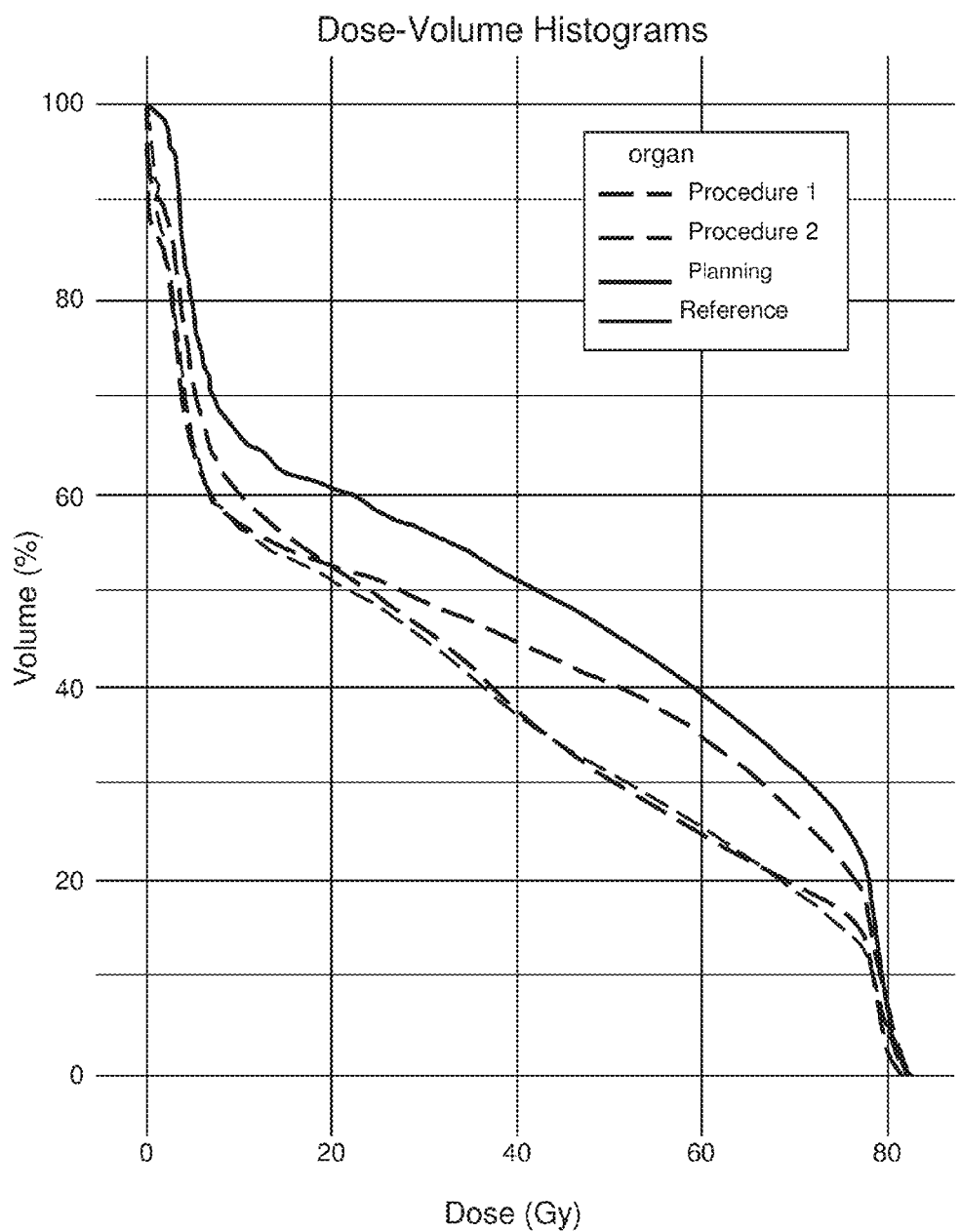
FIG. 5 is an example of comparison of dose-volume histograms obtained according to the invention.

By way of an example, FIG. 5 illustrates a comparison of dose-volume histograms computed on the bladder:
planned DVH 51,
reference aggregate DVH 52,
aggregate DVH estimated by a first commercially available procedure 53,
aggregate DVH estimated by a second commercially available procedure 54.

It can be seen that the results obtained by the first procedure are appreciably superior to those obtained by a second procedure. Thus, the method of the invention determines that this first procedure is the better one whereas intuitively, in relying on the planning curve 51, an observer could have erroneously imagined that the second procedure which is closer to the planning was in all likelihood more efficient.

6.3 Examples of Applications

The invention can be applied to many types of cancer, especially when they relate to deformable organs. In addition to cancer of the prostate, illustrated here above, it can for example be used to evaluate procedures for determining aggregate doses for cancers of the cervix, the uterus, the bladder, the rectum, ENT, etc.

An exemplary embodiment of the invention provides a technique for objectively evaluating the quality and/or precision of a procedure for computing aggregate doses of radiation implemented by a radiotherapy system.

Thus, an embodiment of the invention is not aimed at providing a novel procedure for computing aggregate doses. Rather, it is aimed at providing a tool for evaluating (and if necessary improving) existing procedures of computation as well as future procedures that will be proposed.

An embodiment of the invention is also aimed at providing such a technique for evaluating that is adaptable to numerous organs and especially to deformable organs.

The invention claimed is:

1. A method, implemented by a computing device, for evaluating a procedure for determining an aggregate dose received during a radiotherapy treatment, called a procedure to be evaluated, said procedure to be evaluated being implemented by a treatment device, said method comprising:
    evaluating the procedure for determining an aggregate dose received during a radiotherapy treatment, wherein the evaluating comprises:
    the computing device generating a 3D digital deformable model corresponding to an anatomical region
        by defining the 3D digital deformable model for at least one organ to be treated and at least one neighboring organ, and
        by using said model, generating a series of simulated images interpretable by the procedure to be evaluated;
    the computing device obtaining a reference aggregate dose for said at least one organ to be treated and at least one neighboring organ;
    the procedure to be evaluated delivering, on the basis of at least one image of the series of simulated images, an aggregate dose;
    the computing device delivering at least one piece of information representing quality of said procedure to be evaluated by comparing the reference aggregate dose with the aggregate dose delivered by said procedure to be evaluated,
    said reference aggregate dose being obtained in taking account of anatomical deformations applied to said organs so as to determine a reference dose effectively received by said organs at each treatment session as a function of at least one of their shape or their real position during this session; and
    the computing device improving said procedure for determining the aggregate dose as a function of the comparison of the reference aggregate dose with the aggregate dose delivered by said procedure.

2. The method for evaluating according to claim 1, wherein obtaining said reference aggregate dose includes the following acts:
    generating a model comprising said at least one organ to be treated and said at least one neighboring organ;
    determining a field of deformation of said organs from at least one rule of deformation and/or progress of said organ;
    obtaining a series of images of said model at different instants, called simulated images, comprising at least one image representing a planning scanner and a series of tracking images each corresponding to a session of treatment;
    planning a treatment on the basis of at least one of said simulated images by using a treatment planning system implementing said procedure for determining radiotherapy doses so as to obtain a planned dose and parameters of a set of radiation ballistics;
    determining one set of doses per fraction, each corresponding to one of said sessions; and
    determining said reference aggregate dose in applying said deformation field to each tracking image so as to determine said effectively received reference dose.

3. The method for evaluating according to claim 2, wherein said generating a model delivers a finite-elements model in the form of a 3D mesh.

4. The method for evaluating according to claim 2, wherein said determining a field of deformation implements deformations representing elasticity of each organ, defined by a law of behavior of materials.

5. The method for evaluating according to claim 2, wherein the field of deformation takes account of possible contacts between said organs.

6. The method for evaluating according to claim 2, wherein said act of obtaining a series of simulated images associates, for each simulated image, a view of said model in order to take account of at least bone structure of a corresponding patient.

7. The method for evaluating according to claim 2, wherein, during said act of determining said reference aggregate dose, the dose associated with each tracking image considered is deformed along the field of deformation so as to propagate said dose towards the space of a reference scanner, and all the propagated doses are summed up to obtain the reference aggregate dose.

8. The method for evaluating according to claim 2, wherein said at least one piece of information representing the quality of said method for evaluating belongs to the group consisting of:
  an error of estimation of the aggregate dose at each point of the field of deformation;
  statistical measurements on the errors of estimation of the aggregate dose;
  a representation of the estimated and reference aggregate doses in the form of dose-volume histograms;
  statistical measurements from the dose-volume histograms; and
  differences in terms of indices for evaluating a treatment.

9. The method for evaluating according to claim 1, wherein said organ to be treated belongs to the group consisting of a prostate, a rectum, a bladder and an anal canal.

10. A non-transitory computer-readable medium comprising a computer program product stored thereon, which is comprises program code instructions to execute a method when the instructions are executed on a computer, wherein the method comprises:
  evaluating a procedure for determining an aggregate dose received during a radiotherapy treatment, called a procedure to be evaluated, wherein the evaluating comprises:
  generating a 3D digital deformable model corresponding to an anatomical region
    by defining the 3D digital deformable model for at least one organ to be treated and at least one neighboring organ, and
    by using said model, generating a series of simulated images interpretable by the procedure to be evaluated;
  obtaining a reference aggregate dose for said at least one organ to be treated and at least one neighboring organ;
  the procedure to be evaluated delivering, on the basis of at least one image of the series of simulated images, an aggregate dose;
  delivering at least one piece of information representing quality of said procedure to be evaluated by comparing the reference aggregate dose with the aggregate dose delivered by said procedure to be evaluated,
  said reference aggregate dose being obtained in taking account of anatomical deformations applied to said organs so as to determine a reference dose effectively received by said organs at each treatment session as a function of at least one of their shape or their real position during this session; and
  improving said procedure for determining the aggregate dose as a function of the comparison of the reference aggregate dose with the aggregate dose delivered by said procedure.

11. The non-transitory computer-readable medium according to claim 10, wherein obtaining said reference aggregate dose includes the following acts:
  generating a model comprising said at least one organ to be treated and said at least one neighboring organ;
  determining a field of deformation of said organs from at least one rule of deformation and/or progress of said organ;
  obtaining a series of images of said model at different instants, called simulated images, comprising at least one image representing a planning scanner and a series of tracking images each corresponding to a session of treatment;
  planning a treatment on the basis of at least one of said simulated images by using a treatment planning system implementing said procedure for determining radiotherapy doses so as to obtain a planned dose and parameters of a set of radiation ballistics;
  determining one set of doses per fraction, each corresponding to one of said sessions; and
  determining said reference aggregate dose in applying said deformation field to each tracking image so as to determine said effectively received reference dose.

12. The non-transitory computer-readable medium according to claim 11, wherein said at least one piece of information representing the quality of said method for evaluating belongs to the group consisting of:
  an error of estimation of the aggregate dose at each point of the field of deformation;
  statistical measurements on the errors of estimation of the aggregate dose;
  a representation of the estimated and reference aggregate doses in the form of dose-volume histograms;
  statistical measurements from the dose-volume histograms; and
  differences in terms of indices for evaluating a treatment.

13. A method, implemented by a computing device, for evaluating a procedure for determining an aggregate dose received during a radiotherapy treatment, called a procedure to be evaluated, said procedure to be evaluated being implemented by a treatment device, said method comprising:
  evaluating the procedure for determining an aggregate dose received during a radiotherapy treatment, wherein the evaluating comprises:
  the computing device generating a 3D digital deformable model corresponding to an anatomical region
    by defining the 3D digital deformable model for at least one organ to be treated and at least one neighboring organ, and
    by using said model, generating a series of simulated images interpretable by the procedure to be evaluated;
  the computing device obtaining a reference aggregate dose for said at least one organ to be treated and at least one neighboring organ;
  the procedure to be evaluated delivering, on the basis of at least one image of the series of simulated images, an aggregate dose;

the computing device delivering at least one piece of information representing quality of said procedure to be evaluated by comparing the reference aggregate dose with the aggregate dose delivered by said procedure to be evaluated;

the computing device obtaining said reference aggregate dose by taking account of anatomical deformations applied to said organs so as to determine a reference dose effectively received by said organs at each treatment session as a function of at least one of their shape or their real position during this session, wherein obtaining said reference aggregate dose includes the following acts:

generating a model comprising said at least one organ to be treated and said at least one neighboring organ;

determining a field of deformation of said organs from at least one rule of deformation and/or progress of said organ;

obtaining a series of images of said model at different instants, called simulated images, comprising at least one image representing a planning scanner and a series of tracking images each corresponding to a session of treatment;

planning a treatment on the basis of at least one of said simulated images by using a treatment planning system implementing said procedure for determining radiotherapy doses so as to obtain a planned dose and parameters of a set of radiation ballistics;

determining one set of doses per fraction, each corresponding to one of said sessions; and determining said reference aggregate dose in applying said deformation field to each tracking image so as to determine said effectively received reference dose; and the computing device improving said procedure for determining the aggregate dose as a function of the comparison of the reference aggregate dose with the aggregate dose delivered by said procedure.

* * * * *